United States Patent [19]

Sivilich

[11] Patent Number: 5,669,902

[45] Date of Patent: Sep. 23, 1997

[54] INCONTINENCE GARMENT IN THE FORM OF BOXER SHORTS

[75] Inventor: Daniel M. Sivilich, Freehold Township, N.J.

[73] Assignee: Humanicare International, Inc., North Brunswick, N.J.

[21] Appl. No.: 668,903

[22] Filed: Jun. 24, 1996

[51] Int. Cl.⁶ ........................................ A61F 13/15
[52] U.S. Cl. ................ 604/396; 604/395; 604/397; 604/385.1
[58] Field of Search .................... 604/391, 392, 604/393, 394, 395, 396, 385.1

[56] References Cited

U.S. PATENT DOCUMENTS

| | | | |
|---|---|---|---|
| 1,989,283 | 1/1935 | Limacher | 604/393 |
| 2,859,752 | 11/1958 | Haber | 604/396 |
| 4,114,621 | 9/1978 | Mims, Jr. . | |
| 4,227,531 | 10/1980 | McLeod . | |
| 4,280,230 | 7/1981 | LaFleur . | |
| 4,352,356 | 10/1982 | Tong . | |
| 4,555,245 | 11/1985 | Armbruster . | |
| 4,695,279 | 9/1987 | Steer . | |
| 4,870,958 | 10/1989 | Webster . | |
| 5,052,058 | 10/1991 | Mueller | 604/393 |
| 5,074,854 | 12/1991 | Davis . | |
| 5,291,617 | 3/1994 | Moretz et al. | 604/393 |
| 5,392,467 | 2/1995 | Moretz et al. | 604/393 |
| 5,435,014 | 7/1995 | Moretz et al. . | |
| 5,451,217 | 9/1995 | Fujioka et al. | 604/393 |

*Primary Examiner*—John G. Weiss
*Assistant Examiner*—Ki Yong O
*Attorney, Agent, or Firm*—Robert L. Epstein, Esq.; Harold James, Esq.; James & Franklin

[57] ABSTRACT

The relatively loose fiting external portion of the garment has a waistband. An internal shell is adapted to extend between the legs of the wearer from the front portion of the waistband to the rear portion of the waistband. The shell forms a snug fitting support for an absorbent pad which retains the pad in a position closely adjacent the body. The shell is preferably made of mesh-like elastic material. A liquid impermeable pouch may be attached to the shell to receive the pad in a removeable fashion.

5 Claims, 4 Drawing Sheets

INCONTINENCE GARMENT IN THE FORM OF BOXER SHORTS

The present invention relates to incontinence garments and more particularly to an incontinence garment in the form of boxer shorts.

Literally millions of adults in the United States alone are estimated to suffer from incontinence due to old age or other infirmity. To permit such individuals to lead a more normal life, garments with the capacity to contain waste have been developed.

Many different types and designs of such garments have been used. Plasticized or rubberized garments have been employed, but found to be hot, damp and uncomfortable. A better solution has been found to be a tight fitting knitted fabric brief which carries an absorbent pad. The pad may be permanently affixed to the garment but more practically is removable so that the garment can be washed and reused. While removeability of the pad can be achieved using adhesive strips on the pad, a liquid impermeable pouch which removeably retains the pad is often more desirable. Such a pouch is disclosed in U.S. Pat. No. 4,352,356 issued to David Tong on Oct. 5, 1982 and in U.S. Pat. No. 4,695,279 issued to Graham Steer on Sep. 22, 1987.

Obviously, for the absorbent pad to be effective, it must be retained in a position closely adjacent the body. Accordingly, incontinence garments for men usually take the form of a tight fitting brief. Loose fitting boxer shorts are usually not suitable for this purpose. For that reason, adult men who are incontinent are restricted to use snug fitting briefs because the loose fitting design of boxer shorts makes such boxer shorts ineffective for use with conventional incontinence pads, which require intimate contact with be body to prevent leakage.

However, many men prefer the boxer shorts design because it is loose fitting in the leg area and because of its appearance and style. Until now, there has been no garment in the form of boxer shorts which was capable of providing adequate incontinence protection.

I am aware of U.S. Pat. No. 5,435,014 issued Jul. 25, 1995 to Herbert L. Movetz entitled "Garment Having Suspended Moisture Management Panel" and U.S. Pat. No. 4,555,245 issued to Thomas L. Armbruster on Nov. 26, 1985 entitled "Undergarment with Attached Absorbent Liner". Both teach loose fitting boxer shorts type garments. Both employ absorbent layers of material. However, neither provides support adequate to insure intimate contact of the body with the absorbent layer. Moreover, neither is appropriate for use by patients who suffer from fecal incontinence.

Armbruster teaches a permanently attached internal absorbent liner. One end of the liner is attached to the front panel of the garment. The other end is attached to the crotch section of the garment. Hence, the liner only covers the front of the garment. This structure entirely lacks any means of holding the liner in contact with the body. It is useless for fecal incontinence.

Moretz teaches use of a moisture management panel extending from the front waistband to a point on the back seat. While this structure appears to be an improvement over the Armbruster design, it still does not insure continued contact of the pad with the body. It does not provide for fecal incontinence.

By way of contrast, my invention includes a relatively loose fitting external portion in the form of boxer shorts with a tight fitting internal shell which supports an absorbent pad in a manner which retains the pad in intimate contact with the body. Moreover, my structure permits different size pads to be placed in different positions, so as to be useful for both urinary and fecal incontinence.

It is, therefore, a prime object of the present invention to provide an incontinence garment in the form of boxer shorts. In general, this object is achieved through the use of loose fitting external portion with a tight fitting internal fabric shell. The shell is adapted to extend between the legs and is attached between the front portion of the waistband and the rear position of the waistband. The shell is preferably made of a fabric with some elasticity. It retains an absorbent pad in a position in intimate contact with the body. A liquid impermeable pouch may be affixed to the shell to removeably receive the pad.

More specifically, in accordance with one aspect of the present invention, an incontinence garment is provided including a relatively loose fitting external portion in the form of boxer shorts with an elastic waistband. The waistband has a front portion and a rear portion. An internal fabric shell is provided to support an absorbent pad. The shell is adapted to extend between the legs, from the front portion of the waistband to the rear portion of the waistband. The shell is adapted to retain an absorbent pad which is retained by the shell in a position closely adjacent the body.

Preferably, the shell is made of fabric which is elastic. Such fabric may be mesh. A pouch adapted to receive the pad may be situated on the shell. The pouch is preferably comprised of a sheet of liquid impermeable material.

The pouch has first and second ends which are affixed at spaced locations along the shell. It has a first surface with an opening directed towards the body. It has a second surface facing the shell which is closed.

A vertical front opening with a flap may be employed in the garment. In this way, the garment will have an exterior appearance identical to that of conventional boxer shorts.

In accordance with another aspect of the present invention, an incontinence garment is provided including a relatively loose fitting external portion in the form of boxer shorts with a waistband. The waistband has a front portion and a rear portion. A fabric shell is adapted to extend between the legs of the wearer, from the front portion of the waistband to the rear portion of the waistband. A liquid absorbent pad is provided, as is a liquid impermeable pouch adapted to removeably receive the pad.

The pouch has a first surface with an opening, a second surface which is closed and first and second ends. The first and second pouch ends are affixed at spaced locations along the shell. The first surface faces the body of the wearer. The second section is situated adjacent to and supported by said shell to retain the pad in a position closely adjacent the body.

To these and to such other objects which may hereinafter appear, the present invention relates to an incontinence garment in the form of boxer shorts as set forth in detail in the following specification, and recited in the annexed claims, taken together with the accompanying drawings, wherein like numerals relate to like parts and in which:

Figure 1:
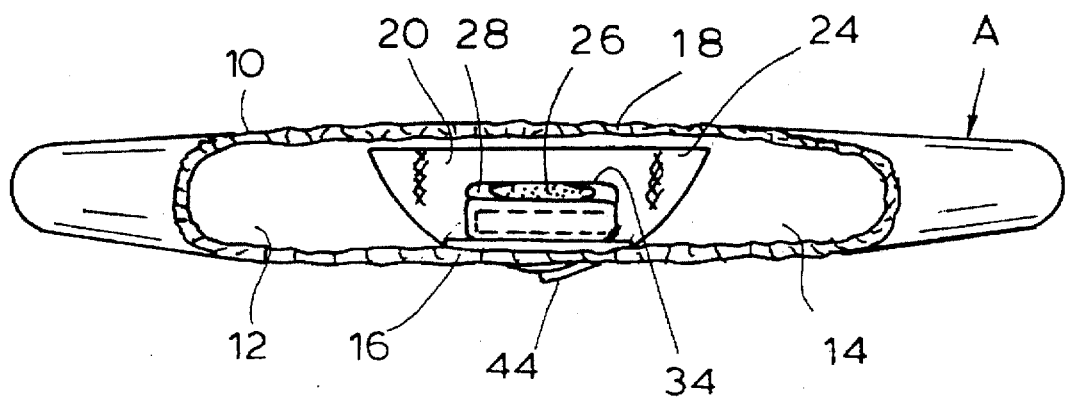
FIG. 1 is a top view of a first preferred embodiment the garment of the present invention.
Figure 2:
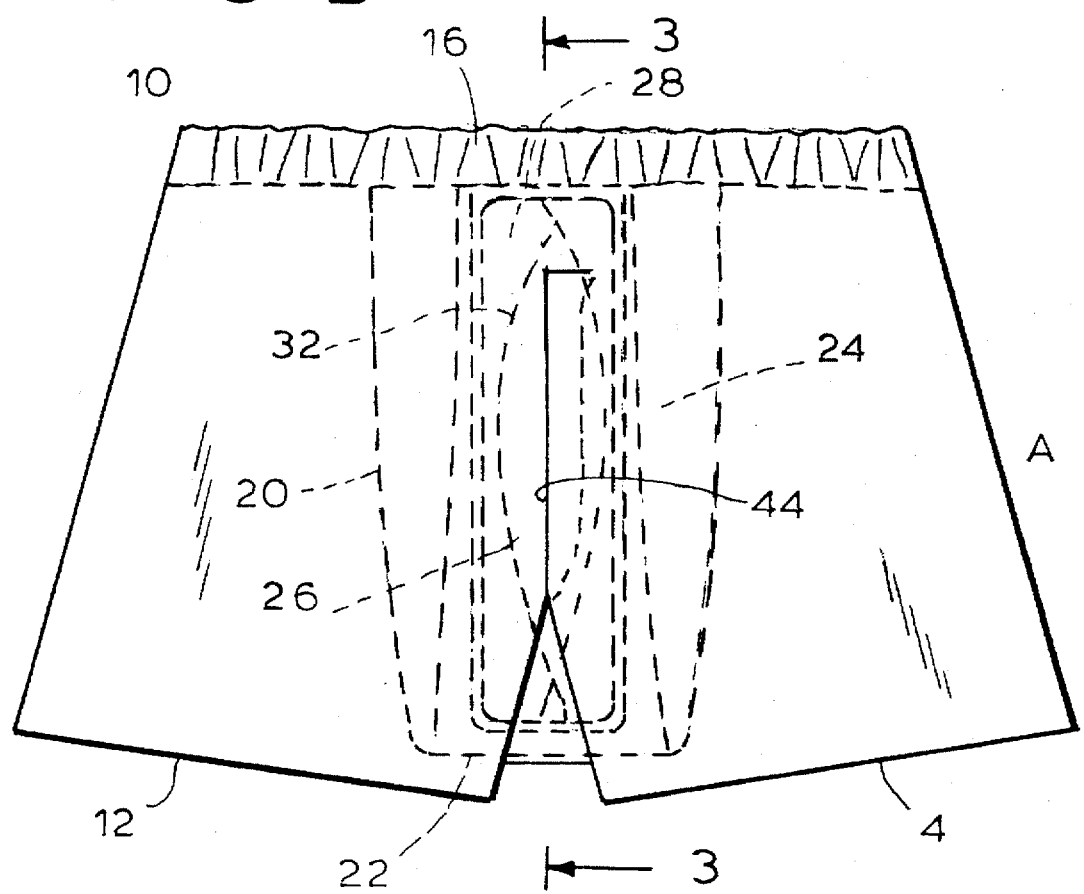
FIG. 2 is a front view of the garment of the FIG. 1.
Figure 3:
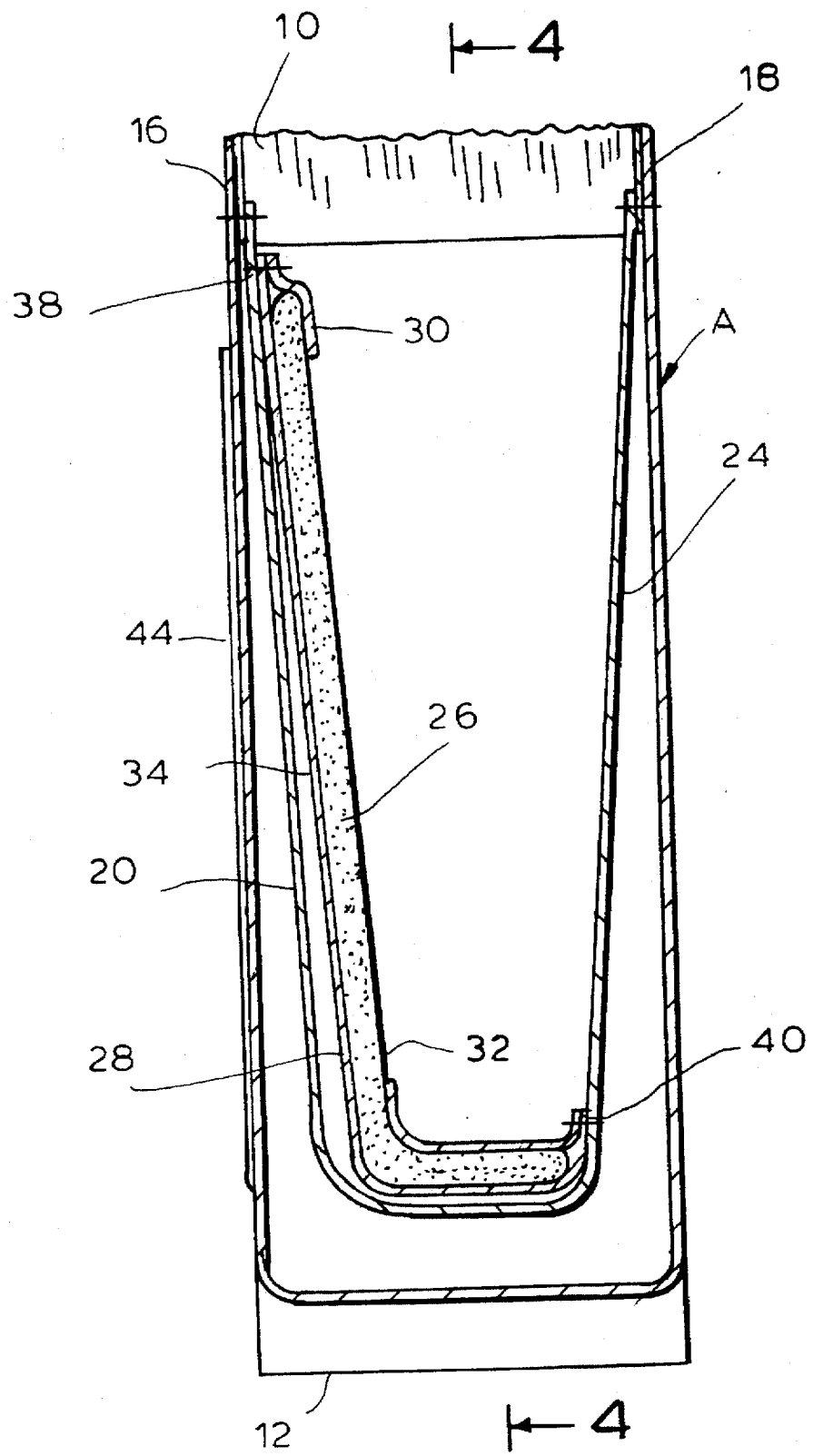
FIG. 3 is a cross-sectional view taken along line 3—3 of FIG. 2.
Figure 4:
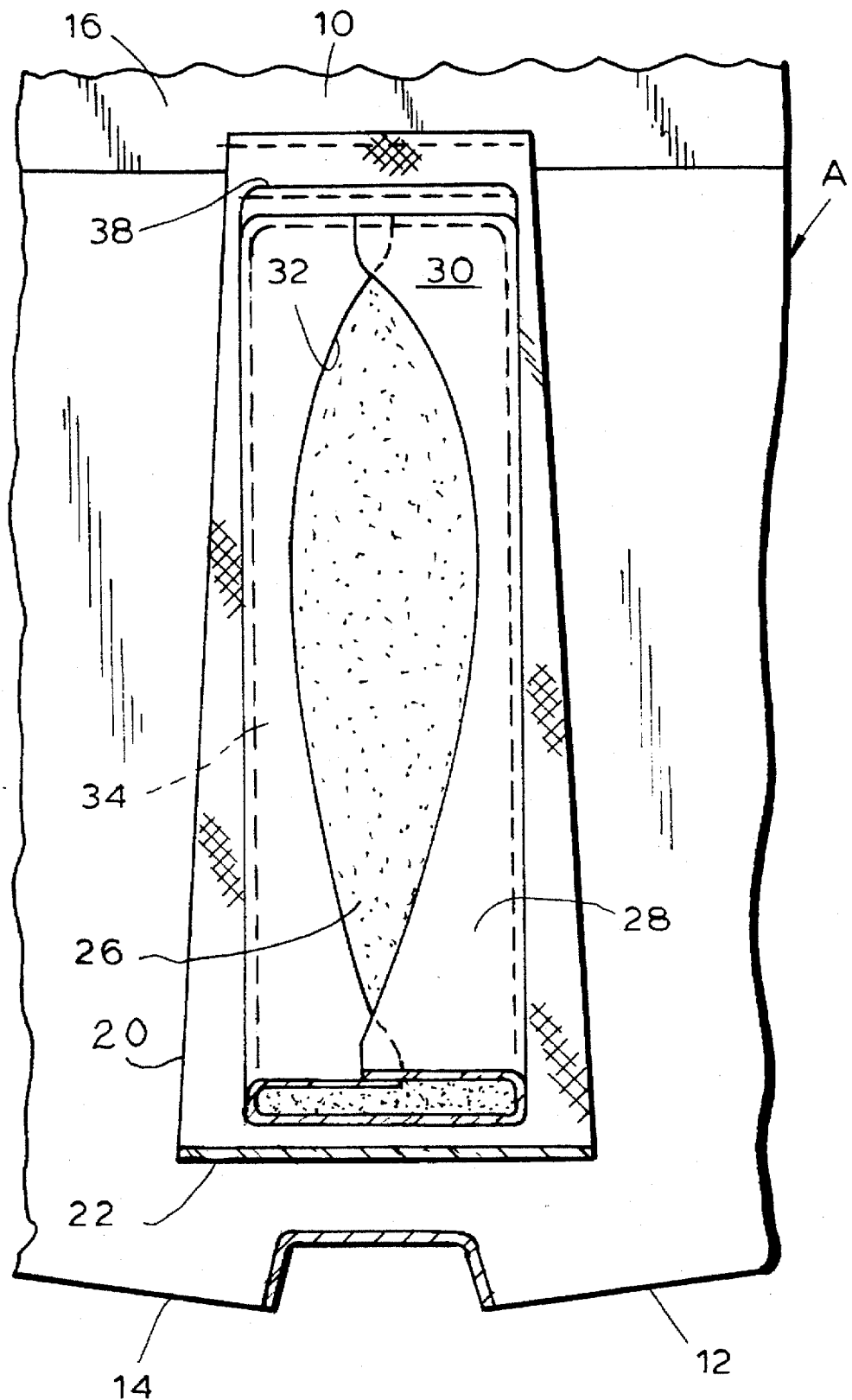
FIG. 4 is a cross-sectional view taken along line 4—4 of FIG. 3.

As seen in the figures, the garment of the present invention comprises an exterior portion corresponding in design to conventional boxer shorts, generally designated A, with an elastic waistband 10 and leg openings 12, 14. Exterior portion A is designed to be loose fitting, particularly in the leg area.

Waistband 10 has a front portion 16 and a rear portion 18. A shell 20 is situated in the interior of the shorts, with one end sewn to waistband portion 16 and the other to waistband portion 18. Shell 20 is formed of a fabric material, preferably with some elasticity. It may be a mesh-like material. The shell has a narrow crotch part 22, adapted to extend between the legs of the wearer and a relatively wider seat part 24.

An absorbent pad 26 of conventional design is situated in the shell. It may be affixed to the shell with adhesive strips or the like. The length and composition of the shell is selected so that the pad is retained in intimate contact with the body.

In the preferred embodiments, a liquid impermeable pouch 28 is provided to retain the pad. Pouch 28 is preferably similar to the design disclosed in the aforementioned Steer U.S. Pat. No. 4,695,379. It is defined by a wall 30 of liquid impermeable material with edges which overlap at the front and the rear to form an oval opening 32 on the top surface. The bottom surface 34 is closed. The edges 36 can be finished with an elastic material to facilitate insertion and removeable of the pad.

Figure 5:
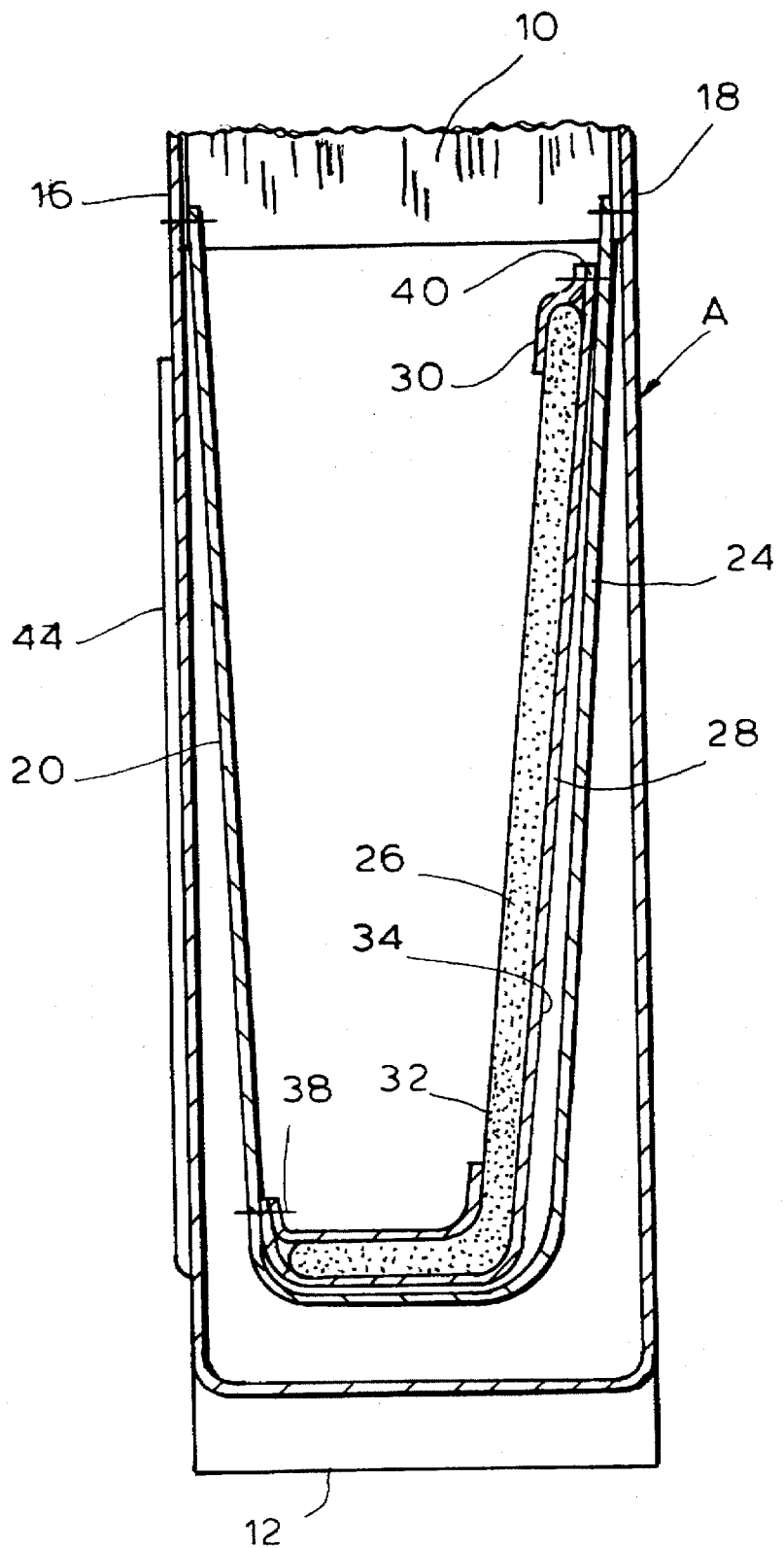
FIG. 5 is a side cross-sectional view of a second preferred embodiment of the present invention.

The ends 38, 40 of the pouch are sewn to shell 20 at spaced locations. The placement of the pouch 28 relative to the shell depends upon whether the garment is for urinary or fecal protection. Urinary protection is achieved with the pouch located as shown in FIGS. 1–4. Lengthing the pad and pouch and/or moving the pouch to a position aligned with section 24 will provide fecal protection, as shown in FIG. 5.

The invention may be provided with a front vertical opening 42 covered by a flap 44, as is conventional with boxer shorts. In this way, the garment will appear from the exterior to be the same as conventional boxer shorts.

It will now be appreciated that the present invention relates to an incontinence garment in the form of boxer shorts. The boxer shorts are provided with an internal fabric shell extending from the front waistband to the rear waistband, preferably of elastic material, designed to maintain an absorbent pad in intimate contact with the body. A liquid impermeable pouch may be affixed to the shell to removeably retain the pad.

While only two preferred embodiments have been disclosed herein for purposes of illustration, it is obvious that many modifications and variations could be made thereto. It is intended to cover all of these modifications and variations which fall within the scope of the invention, as defined by the following claims:

I claim:

1. An incontinence garment adapted to be worn on a body with legs, said garment comprising an exterior portion in the form of boxer shorts with a waistband, said waistband having a front portion and a rear portion, an internal elastic shell comprising a front part attached to said front waistband portion, a crotch part adapted to extend between the legs and a relatively wider seat part attached to said second waistband portion, a liquid absorbent pad, a pouch adapted to removeably receive said pad, said pouch having a first surface with an opening, a second substantially liquid impermeable surface and first and second ends, said first and second ends being affixed at spaced locations along said shell, said first surface facing the body and said second surface supported by said shell, such that said pad is retained closely adjacent to the body.

2. The garment of claim 1 wherein said shell is composed of elastic material.

3. The garment of claim 1 wherein one of said pouch ends is proximate one of said waistband portions.

4. The garment of claim 1 wherein said first pouch end is proximate said first waistband portion.

5. The garment of claim 1 wherein said second pouch end is proximate said second waistband portion.

* * * * *